United States Patent [19]

Waring

[11] 4,205,087
[45] May 27, 1980

[54] ACETIC ACID DERIVATIVES

[75] Inventor: Wilson S. Waring, Macclesfield, England

[73] Assignee: Imperial Chemical Industries Limited, London, England

[21] Appl. No.: 790,873

[22] Filed: Apr. 26, 1977

[30] Foreign Application Priority Data

May 21, 1976 [GB] United Kingdom ............... 21064/76

[51] Int. Cl.$^2$ .................... A61K 31/19; A61K 31/215
[52] U.S. Cl. ............................... 424/317; 260/559 D; 560/57; 560/58; 562/468; 424/308; 424/324
[58] Field of Search ................ 260/520 B; 560/57, 58; 562/468; 424/308, 317

[56] References Cited

U.S. PATENT DOCUMENTS

| 3,637,827 | 1/1972 | Kaiser et al. ..................... 260/520 B |
| 4,003,932 | 1/1977 | Gootjes ................................. 560/57 |

FOREIGN PATENT DOCUMENTS 124738  4/1949  Sweden.

OTHER PUBLICATIONS

Van der Steet et al, Recl. Trav. Chem. Pays–Bas, 1973, (92/4), pp. 493–512 (1973).

Primary Examiner—Jane S. Myers
Attorney, Agent, or Firm—Cushman, Darby & Cushman

[57] ABSTRACT

Novel di-(substituted phenyl)methoxy acetic acids, alkyl homologues and related salts, ester and amides thereof, together with processes for their manufacture, and pharmaceutical compositions. A representative compound is di-(4-chlorophenyl)methyloxy acetic acid. The compounds possess anti-arthritic properties and in some cases, in addition, an effect on a factor involved in atherosclerotic disease.

4 Claims, No Drawings

ACETIC ACID DERIVATIVES

This invention relates to acetic acid derivatives and more particularly it relates to acetic acid derivatives which possess anti-arthritic properties. In addition, certain of the acetic acid derivatives also have an effect on at least one of the factors involved in atherosclerotic disease.

According to the invention there is provided an acetic acid derivative of the formula:

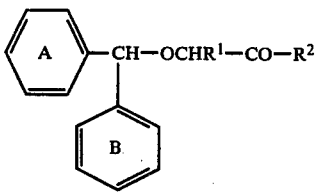

I wherein $R^1$ is hydrogen or a methyl radical; $R^2$ is a hydroxy, amino or dialkylamino radical of 2 to 8 carbon atoms, or a $C_{1-6}$-alkoxy radical optionally bearing as a substituent a $C_{1-4}$-alkoxy radical or a dialkylamino radical of 2 to 8 carbon atoms; and ring A and ring B, which may be the same or different, optionally bear one or two halogen atoms or trifluoromethyl radicals as substituents, provided that ring A and ring B taken together bear at least two halogen atom substituents; or a pharmaceutically acceptable base-addition salt of a compound of formula I wherein $R^2$ is a hydroxy radical; or a pharmaceutically acceptable acid-addition salt of a compound of formula I wherein $R^2$ is a $C_{1-6}$-alkoxy radical bearing as a substituent a dialkylamino radical of 2 to 8 carbon atoms.

It will be readily apparent that certain compounds of formula I, for example those wherein $R^1$ is a methyl radical, contain an asymmetric carbon atom and can thus be isolated in a racemic form and in two optically active forms. It is to be understood that this specification encompasses the racemic form of those compounds of formula I which contain an asymmetric carbon atom and any optically active form which possesses the above useful properties; it being a matter of general knowledge in the art how to obtain the optically active forms and to determine their biological properties.

A particular value for $R^2$ when it is a dialkylamino radical of 2 to 8 carbon atoms is, for example, a dimethylamino or diethylamino radical.

A particular value for $R^2$ when it is a $C_{1-6}$-alkoxy radical is, for example, a methoxy, ethoxy, propoxy or butoxy radical.

A particular value for a dialkylamino radical of 2 to 8 carbon atoms, when present as a substituent when $R^2$ is a $C_{1-6}$-alkoxy radical, is, for example, a dimethylamino or diethylamino radical.

A particular value for a $C_{1-4}$-alkoxy radical, when present as a substituent when $R^2$ is a $C_{1-6}$-alkoxy radical, is, for example, a methoxy or ethoxy radical.

Particularly suitable values for $R^2$ are, for example, hydroxy, amino, dimethylamino, diethylamino, methoxy, ethoxy and 2-ethoxyethoxy radicals.

A particular value for a halogen atom substituent on ring A or B is, for example, a fluorine, chlorine or bromine atom.

Particular values for ring A and ring B are, for example, phenyl, 4-chlorophenyl, 2-chlorophenyl, 4-fluorophenyl, 4-bromophenyl, 2,4-dichlorophenyl and 4-chloro-3-trifluoromethylphenyl radicals.

Particularly suitable combinations of ring A and ring B are, for example, when both ring A and ring B are monohalogenophenyl radicals, for example monochlorophenyl radicals; or when ring A is a dihalogenophenyl radical, for example a 2,4-dichlorophenyl radical, and ring B is a phenyl radical.

A particular group of compounds of the invention comprises those compounds of formula I wherein both ring A and ring B are identical mono-halogenophenyl radicals, $R^1$ is hydrogen and $R^2$ is a hydroxy radical; together with the base-addition salts thereof.

Specific compounds of the invention are described in the accompanying Examples and of these particularly preferred compounds of formula I are di-(4-chlorophenyl)methyloxyacetic acid, together with its 2-ethoxyethyl ester and its pharmaceutically acceptable base-addition salts; and di-(2-chlorophenyl)methoxyacetic acid, together with its pharmaceutically acceptable base-addition salts.

A particular base-addition salt of a compound of formula I wherein $R^2$ is a hydroxy radical is, for example, an alkali metal or alkaline earth metal salt, for example, a sodium, potassium, calcium or magnesium salt, an aluminium salt, for example an aluminium hydroxide di-salt, or a salt with an organic base affording a pharmaceutically acceptable cation, for example triethanolamine or benzylamine.

A particular acid-addition salt of a compound of formula I, wherein $R^2$ is an alkoxy radical bearing a dialkylamino radical, is, for example, a salt with an inorganic acid, for example hydrochloric or sulphuric acid, or with an organic acid affording a pharmaceutically-acceptable anion, for example oxalic acid or maleic acid.

The compounds of the invention may be administered in the form of a pharmaceutical composition and according to a further feature of the invention there is provided a pharmaceutical composition comprising an acetic acid derivative of formula I or a pharmaceutically acceptable salt thereof in association with a pharmaceutically acceptable diluent or carrier.

The composition may be in a form suitable for oral administration, for example in the form of a tablet, capsule, aqueous suspension, oily solution or suspension, emulsion, dispersible powder, granule, syrup or elixir; or for parenteral administration, for example in the form of a sterile injectable aqueous suspension or oily solution or suspension; or for rectal administration, as a suppository.

Compositions intended for oral use may be prepared by known general means and may contain one or more agents selected from sweetening agents, for example sucrose; flavouring agents, for example essential oils; and colouring agents, in order to provide an elegant and palatable preparation.

The tablets may contain the active ingredient in admixture with conventional pharmaceutical excipients, for example, inert diluents, granulating and disintegrating agents, binding agents, and lubricating agents, for example magnesium stearate. The tablets may be uncoated or they may be coated by known techniques to increase stability or to mask unpalatable taste. They may also be formulated so as to delay disintegration and absorption in the gastro-intestinal tract and thereby provide a sustained action over a longer period.

Formulations for oral use may also be presented as hard gelatin capsules containing the active ingredient alone, or containing the active ingredient in admixture with an inert solid diluent. Alternatively, they may be presented as soft gelatin capsules wherein the active ingredient is mixed with an oily medium.

The aqueous suspensions may contain the active ingredient in admixture with conventional pharmaceutical excipients, for example, suspending agents, and dispersing or wetting agents.

The pharmaceutical composition may also be in the form of an oil-in-water emulsion or oily suspension in which the oily phase may be a vegetable or mineral oil, or a mixture of these. A suitable anti-oxidant or emulsifying agent may also be present.

Dispersible powder and granules suitable for the extemporaneous preparation of an aqueous suspension by the addition of water may contain the active ingredient in admixture with a dispersing or wetting agent, suspending agent and one or more preservatives.

Syrups and elixirs may be formulated with sweetening agents, and may also contain a demulcent, a preservative and flavouring and colouring agents.

Compositions intended for parenteral administration may be sterilized by conventional methods.

The pharmaceutical composition may alternatively be in the form of a suppository intended for administration of the active ingredient per rectum. Such a composition may be prepared by mixing the active ingredient with a conventional non-irritating excipient which is solid at ordinary temperatures but liquid at the rectal temperature and will therefore melt in the rectum to release the active ingredients.

The compounds of formula I may be manufactured by any process which is applicable to the manufacture of chemically analogous compounds. Such processes are provided as a further feature of the invention and are exemplified by the following wherein $R^1$, $R^2$, ring A and ring B have the meanings defined above, unless specifically stated otherwise.

(a) Reacting a salt of a benzhydrol of the formula:

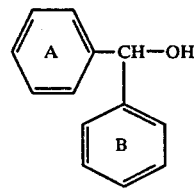

II with a compound of the formula:

Hal.—$CHR^1$—CO—$R^2$    III wherein Hal. is a chlorine, bromine or iodine atom and, preferably, a bromine or iodine atom.

A particularly convenient salt of a derivative of formula II is, for example, an alkali metal salt for example a sodium or a potassium salt. This salt may either be pre-formed from a derivative of formula II and a suitable base, and this is preferred, or it may be formed in the reaction itself by including a suitable base in the reaction mixture.

A particularly suitable base is, for example, an alkali metal hydride or $C_{1-4}$-alkoxide, for example sodium or potassium hydride or ethoxide.

The reaction or salt formation may be conveniently carried out in an inert organic solvent, for example dimethylformamide, or a mixture of such solvents, and at a temperature of, for example 10°-100° C., preferably at, for example, 20°-30° C. for an extended period. A particularly convenient solvent when an alkali metal $C_{1-4}$-alkoxide is used as base is, for example, the corresponding $C_{1-4}$-alkanol, for example ethanol when an ethoxide is used as base.

(b) For a compound of formula I $R^2$ is other than a hydroxy radical, reacting a compound of the formula I wherein $R^2$ is a hydroxy radical, that is a carboxylic acid of formula I or a reactive derivative thereof, with a compound of the formula $R^3.H$ wherein $R^3$ has the meaning defined above for $R^2$ other than a hydroxy radical.

A particularly suitable reactive derivative of a carboxylic acid of formula I is, for example, an acid halide, for example an acid chloride, an acid azide, an acid anhydride, or a mixed acid anhydride derived from a carboxylic acid of formula I and formic acid or a $C_{2-4}$-alkanoic acid, for example acetic acid.

When a reactive derivative is used, the reaction is preferably carried out in the presence of a base, for example pyridine or triethylamine and, conveniently in an inert solvent or diluent, for example chloroform, methylene chloride or diethyl ether, and at a temperature of, for example, 0°-100° C.

The starting material of the formula $R^3.H$ may conveniently be employed in an excess, and when it is a liquid, it may serve as a solvent instead of, or in addition to, the inert solvent or diluent defined above.

(c) For a compound of formula I wherein $R^2$ is an optionally substituted $C_{1-6}$-alkoxy radical, reacting a salt of a compound of formula I wherein $R^2$ is a hydroxy radical, that is of an acid of formula I, with a compound of the formula $R^4$-Hal., wherein $R^4$ is a $C_{1-6}$-alkyl radical optionally bearing as a substituent a $C_{1-4}$-alkoxy radical or a dialkylamino radical of 2 to 8 carbon atoms and Hal. is a chlorine, bromine or iodine atom.

A particular value for $R^4$ when it is a $C_{1-6}$-alkyl radical is, for example, a methyl, ethyl, propyl or butyl radical. Particular values for the optional substituent which may be present on $R^4$ are those stated above for the optional substituent which may be present when $R^2$ is an alkoxy radical.

A particularly convenient salt of a carboxylic acid of formula I used as starting material is, for example, an alkali metal salt, for example a sodium or a potassium salt, which may conveniently be pre-formed by reacting a carboxylic acid of formula I with a base, for example, sodium hydride or potassium hydride. The reaction may conveniently be carried out in an inert organic solvent or diluent, for example dimethyl formamide, and at, for example, 0°-100° C. and preferably, at 15°-30° C.

(d) For a compound of formula I wherein $R^2$ is a hydroxy radical, hydrolysing a compound of the formula:

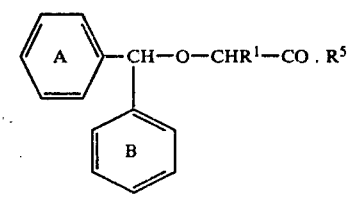

IV wherein $R^5$ is a $C_{1-6}$-alkoxy, benzyloxy or phenoxy radical.

A particularly suitable $C_{1-6}$-alkoxy radical is, for example, a methoxy or ethoxy radical.

The hydrolysis may be carried out, in the presence of a strong base, for example sodium or potassium hydroxide, or in the presence of mineral acid, for example hydrochloric acid.

The reaction is conveniently performed in the presence of an organic solvent or diluent, for example ethanol or methanol, optionally mixed with water. The hydrolysis may be conveniently carried out, for example, at the boiling point of the reaction mixture. The necessary starting materials of formula IV may be made by process (a) or (b) hereinabove.

(e) For a compound of formula I wherein $R^2$ is a dialkylamino radical of 2 to 8 carbon atoms or an amino radical, reacting a compound of formula IV wherein $R^5$ has the meaning defined in respect to process (d), with an amine of the formula $R^6.H$ wherein $R^6$ is a dialkylamino radical of 2 to 8 carbon atoms or an amino radical.

Particularly suitable values for the dialkylamino radical $R^6$ are those defined hereinbefore for $R^2$ when it is such a radical.

The amine of the formula $R^6.H$ is conveniently employed in an excess and the reaction is preferably carried out in the presence of an organic solvent or diluent, for example a $C_{1-4}$-alkanol, for example ethanol, conveniently, for example, at the boiling point of the reaction mixture. When the amine of the formula $R^6.H$ is volatile, the reaction is preferably carried out in a sealed system.

Whereafter, when a base-addition salt is required, a compound of formula I wherein $R^2$ is a hydroxy radical is reacted in a conventional manner with a suitable base as defined above; and when an acid-addition salt is required, a compound of formula I which is sufficiently basic is reacted conventionally with a suitable acid as defined above.

The remaining starting materials required for the above processes may be made according to generally known procedures of organic chemistry.

The anti-arthritic properties of the compounds of formula I may be demonstrated by their effect in inhibiting the increase in the thickness of a rat's foot injected with dead turbercle bacilli when administered over 14–21 days, essentially according to the standard test procedure of Newbould (*Brit. J. Pharmacol.*, 1963, 21, 127–136), and also by their effect in inhibiting the increase in the concentration of $\alpha_1$-acid glycoprotein in the blood serum of the rats used in this test. In general compounds of formula I show significant activity in this test at a dose of 50 mg./kg. or less, without any overt toxic effects being observed at the active dose.

When used to produce anti-arthritic effects in warm blooded animals, the compounds of the invention may be administered orally so that a daily dose of from 20 to 100 mg./kg. of a compound of formula I is received. In man this is equivalent to a total daily dose of from 500 to 2500 mg. of a compound of formula I given, if necessary, in divided doses.

In addition to anti-arthritic properties, certain compounds of formula I have a desirable influence on one or more of the factors involved in atherosclerotic disease. These factors are elevated concentrations of cholesterol, total esterified fatty acids and fibrinogen in the blood plasma, and some of the compounds of formula I, for example di-(4-chlorophenyl)methyloxyaceticacid, are capable of lowering the concentration of at least one member of the above group of blood plasma components in warm blooded animals. This property may be demonstrated in standard tests by the effect of the compounds in lowering the concentration of the relevant blood plasma component to at least 80% of the control value when administered orally to rats over a period of 7 to 14 days, or by their activity, or that of the corresponding acid, in vitro, in displacing thyroxine from human albumin when present in an equimolar amount relative to the albumin. In this test an increase in the amount of unbound thyroxine similar to that produced by 2-(4-chlorophenoxy)-2-methylpropionic acid is considered to represent highly significant activity. In these tests, no overt toxic effects were noticed at the active dose.

When used to lower the concentrations of the above blood plasma components in warm blooded animals, the compounds of the invention may be administered orally so that a daily dose of from 10 to 200 mg./kg. of a compound of formula I is received. In man this is equivalent to a total daily dose of 0.25 to 5 g. of a compound of formula I given, if necessary, in divided dose.

Compositions intended for use in the treatment of atherosclerotic disease may also contain other agents which can have a beneficial effect on the disease or associated conditions, for example nicotinyl alcohol, nicotinic acid or a salt thereof, raubasine, vitamin E, an anion exchange resin, for example cholestyramine, colestipol or a dialkylaminoalkyl derivative of a cross-linked dextran, or a calcium or magnesium salt, or metformin or phenformin.

Compositions intended for use in the treatment of arthritis or related joint diseases may also contain other agents having anti-inflammatory or analgesic activity, for example, acetyl salicylic acid, paracetamol, dextropropoxyphene, codeine, chloroquine, phenylbutazone, D-penicillamine, indomethacin, ibuprofen, ketoprofen or naproxen, or an anti-inflammatory steroid, for example prednisolone, or an organogold derivative, or a uricosuric agent, for example probenecid.

The invention is illustrated, but not limited, by the following Examples in which:

(i) all evaporations were carried out by rotary evaporation in vacuo, (ii) all temperatures refer to the Centigrade scale, (iii) petroleum ether, b.p. 60°–80° C., is specified as "petrol"

(iv) ambient temperature refers to a temperature in the range 18°–25° C., and (v) yields where given are purely illustrative and are not to be construed as the maximum attainable for the process illustrated.

EXAMPLE 1

Sodium hydride (1.0 g., 80% w/w suspension in mineral oil) was added gradually to a stirred solution of 4,4'-dichlorobenzhydrol (7.5 g.) in dry dimethylformamaide keeping the temperature below 30°. After 30 minutes stirring ethyl bromoacetate (4.0 ml.) was then added keeping the temperature below 30°. After 3 hours stirring at ambient temperature the mixture was poured into water (100 ml.) and the subsequent mixture was extracted with ether. The combined extracts were washed with water, dried (MgSO$_4$) and evaporated. The residual oil was added to a column of dry chromatoraphic silicagel [500 g., previously deactivated by addition of 10% w/w water and then equilibrated with 10% v/w of a mixture of toluene and acetone (10:1 v/v)]. The column was then eluted with the same mixture of toluene and acetone to give, after evaporation of solvent, ethyl di-(4-chlorophenyl)methyloxyacetate as an oil, in 90% yield, and having the following characteristic NMR spectrum (in CDCl₃; chemical shifts in δ values):

1.28 (triplet, 3 protons, —CO₂CH₂C$\underline{H}_3$),
4.15 (singlet, 2 protons, —OC$\underline{H}_2$OC—),
4.30 (quartet, 2 protons, —CO₂C$\underline{H}_2$CH₃),
5.66 (singlet, 1 proton, >C$\underline{H}$OCH₂),
7.47 (singlet, 8 aromatic protons).

EXAMPLE 2

A mixture of crude ethyl di-(4-chlorophenyl)methyloxyacetate (9 g.), sodium hydroxide (5 g.), ethanol (150 ml.) and water (5 ml.) was heated under reflux for 16 hours. The mixture was evaporated and the residue was diluted with water (100 ml.) and ether (30 ml.). The ether extracts were discarded and the aqueous phase was acidified to pH 2-3 with 20% v/v hydrochloric acid. The mixture was extracted with ether and the extracts were dried (MgSO₄) and evaporated. The residual solid obtained was crystallised from a mixture of ethyl acetate and petrol to give di-(4-chlorophenyl)methyloxyacetic acid, m.p. 108°–110°, in 64% yield.

EXAMPLE 3–6

The process described in Example 1 was repeated using the appropriate benzhydrol of formula II and a bromoester of the formula:

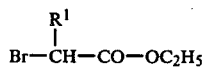

instead of 4,4'-dichlorobenzhydrol and ethylbromoacetate respectively. There were thus obtained the following esters of the formula:

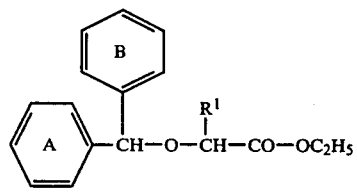

| Example No. | Ring A | Ring B | R¹ | % Yield |
|---|---|---|---|---|
| 3 | 4-chlorophenyl | 4-chlorophenyl | CH₃ | 82% |
| 4 | 4-fluorophenyl | 4-fluorophenyl | H | 70% |
| 5 | 2-chlorophenyl | 2-chlorophenyl | H | 81% |
| 6 | 2,4-dichlorophenyl | phenyl | H | 80% |

EXAMPLES 7–10

The process described in Example 2 was repeated using an ester obtained in any one of Examples 3–6 in place of ethyl di-(4-chlorophenyl)methyloxyacetate as starting material. There was thus obtained a carboxylic acid of the formula:

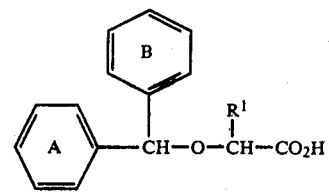

| Ex. No. | Ring A | Ring B | R¹ | % Yield | m.p. (°C.) | Crystallisation solvent(s) |
|---|---|---|---|---|---|---|
| 7 | 4-chlorophenyl | 4-chlorophenyl | CH₃ | 67 | 166–168 | Ethyl acetate or toluene |
| 8 | 4-fluorophenyl | 4-fluorophenyl | H | 47 | 91–93 | Toluene |
| 9 | 2-chlorophenyl | 2-chlorophenyl | H | 64 | 169–171 | Ethyl acetate |
| 10 | 2,4-dichlorophenyl | phenyl | H | 85 | 119–120* | Ethyl acetate |

*This acid was isolated as an oil and was characterised as its benzylamine salt.

EXAMPLE 11

Sodium hydride (1.32 g., 80% w/w dispersion in mineral oil) was added in portions to a solution of di-(4-chlorophenyl)methyloxyacetic acid (6.2 g.) in dry dimethylformamide (30 ml.) cooled below 30°. The mixture was stirred for 15 minutes at ambient temperature after the addition was complete and N,N-dimethyl-2-chloroethylamine hydrochloride (2.88 g.) was then added. The mixture was heated at 100° for 16 hours, cooled and then poured into water (200 ml.). The aqueous mixture was extracted with ether. The extracts were washed with aqueous acetic acid (2×100 ml. of a 10% v/v solution). The acid washings were basified to pH 11–12 with aqueous sodium hydroxide solution and extracted with ether. The ether extracts were dried (MgSO₄) and evaporated. The residual oil thus obtained was mixed with an excess of an ethereal solution of maleic acid. The solid thus formed was separated by filtration and crystallised from ethyl acetate to give 2-dimethylamino-ethyl di-(4-chlorophenyl)methyloxyacetate as the maleate salt, m.p. 103°–104°, having the composition C₁₉H₂₁O₃NCl₂.C₄H₄O₄ by microanalysis, and in 43% yield.

EXAMPLE 12

The process described in Example 1 was repeated using N,N-diethyl chloroacetamide instead of ethyl bromoacetate. There was thus obtained N,N-diethyl di-(4-chlorophenyl)methyloxyacetamide as a colourless oil, in 55% yield, and having the following characteristic NMR spectrum (in CDCl₃; chemical shifts in δ values):

1.10 (triplet, 6 protons, CONCH₂C$\underline{H}_3$),
3.30 (quartet, 4 protons, CONC$\underline{H}_2$CH₃),
4.10 (singlet, 2 protons, OC$\underline{H}_2$CO),
5.55 (singlet, 1 proton, C$\underline{H}$O),
7.26 (singlet, 8 aromatic protons)

EXAMPLE 13

The process described in Example 1 was repeated using 4,4'-dibromobenzhydrol instead of 4,4'-dichlorobenzhydrol. There was thus obtained ethyl di-(4-bromophenyl)methyloxyacetate as a colourless oil in 75% yield.

EXAMPLE 14

The process described in Example 2 was repeated using ethyl di-(4-bromophenyl)methyloxyacetate as starting material, and there was thus obtained di-(4-bromophenyl)methyloxyacetic acid, m.p. 124°–126° (after crystallisation from toluene), in 61% yield.

EXAMPLE 15

The process described in Example 1 was repeated using 4,4'-dichloro-3-trifluoromethylbenzhydrol instead of 4,4'-dichlorobenzhydrol. There was thus obtained ethyl-(4-chlorophenyl) (4-chloro-3-trifluoromethylphenyl)methyloxyacetate as an oil, in 34% yield, and having the following characteristic NMR spectrum (in $CDCl_3$; chemical shifts in $\delta$ values):
1.30 (triplet, 3 protons, $CO_2CH_2\underline{CH}_3$),
4.20 (singlet, 2 protons, $O\underline{CH}_2CO$),
4.35 (quartet, 2 protons, $CO_2\underline{CH}_2CH_3$),
5.74 (singlet, 1 proton, $>C\underline{H}O$),
7.3–8.0 (multiplet, 7 aromatic protons).

EXAMPLE 16

Sodium hydride (0.65 g., 80% w/w dispersion in mineral oil) was added in portions to a solution of di-(4-chlorophenyl)methyloxyacetic acid (6.2 g.) in dry dimethylformamide (20 ml.) cooled below 30°. The mixture was stirred for 15 minutes at ambient temperature after addition was complete and 1-bromo-2-ethoxyethane (3 g.) was then added. The mixture was heated at 80° for 16 hours, cooled and then poured into water (200 ml.). The aqueous mixture was extracted with ether, and the ether solution washed successively with water, dilute ammonium hydroxide, and then water, dried ($MgSO_4$) and evaporated. The residual oil (5.1 g.) was purified by dry column chromatography on deactivated silica-gel (500 g.) as described in Example 1 but using toluene as solvent instead of a mixture of toluene and acetone. The column was eluted with toluene to give, after evaporation of solvent, 2-ethoxyethyl di-(4-chlorophenyl)methyloxyacetate as a colourless oil, in 67% yield, and having the following characteristic NMR spectrum (in $CDCl_3$; chemical shifts in $\delta$ values):
1.19 (triplet, 3 protons, $OCH_2\underline{CH}_3$),
3.52 (quartet, 2 protons, $O\underline{CH}_2CH_3$),
3.64 (multiplet, 2 protons, $CO_2CH_2\underline{CH}_2O$),
4.28 (multiplet, 2 protons, $CO_2\underline{CH}_2CH_2O$),
4.12 (singlet, 2 protons, $O\underline{CH}_2CO$),
5.56 (singlet, 1 proton, $C\underline{H}O$),
7.30 (singlet, 8 aromatic protons).

EXAMPLE 17

The process described in Example 1 was repeated except that methyl chloroacetate was used instead of ethylbromoacetate. There was thus obtained methyl di-(4-chlorophenyl)methyloxyacetate as a colourless oil in 65% yield.

EXAMPLE 18

Methyl di-(4-chlorophenyl)methyloxyacetate (5 g.) was heated in a sealed tube with a saturated solution of ammonia in methanol (20 ml.) at 130° for 6 hours. The solution was evaporated to dryness under reduced pressure and the residue rubbed with petrol and filtered. The solid residue was crystallised from a mixture of ethyl acetate and petrol and there was thus obtained di-(4-chlorophenyl)methyloxyacetamide, m.p. 112°–113°, in 26% yield.

EXAMPLE 19

A mixture of 50 parts by weight of di-(4-chlorophenyl)methyloxyacetic acid, 27 parts by weight of lactose, and 20 parts by weight of maize starch was thoroughly stirred, and a paste formed from 2 parts by weight of maize starch and 40 parts by weight of water was added and thoroughly mixed. The resulting mass was passed through a 16-mesh screen, dried at 60° to constant weight and then passed through a 20 mesh screen. 1 Part by weight of magnesium stearate was added to the granules thus obtained and the mixture was compressed by conventional means, into tablets containing 50, 100, 250 or 500 mg. of active ingredient, suitable for oral administration for therapeutic purposes.

In a similar manner, the active ingredient in the above procedure may be replaced by another compound of formula I, for example as described in Example 1 or in any one of Examples 3–18, to give tablets suitable for oral administration for therapeutic purposes.

EXAMPLE 20

A mixture of 50 parts by weight of di-(4-chlorophenyl)methyloxyacetic acid, 33 parts by weight of calcium phosphate, 10 parts by weight of microcrystalline cellulose and 4 parts by weight of calcium carboxymethylcellulose was thoroughly stirred and a paste formed from 2 parts by weight of polyvinylpyrrolidone and 40 parts by weight of water was added and thoroughly mixed. The resulting mass was passed through a 16-mesh screen, dried at 60° to constant weight and then passed through a 20-mesh screen. 1 Part by weight of magnesium stearate was added to the granules thus obtained and the mixture was compressed, by conventional means, into tablets containing 50, 100, 250 or 500 mg. of active ingredient, suitable for oral administration for therapeutic purposes.

In a similar manner, the active ingredient in the above procedure may be replaced by another compound of formula I as described in Example 1 or in any one of Examples 3–18, to give tablets suitable for oral administration for therapeutic purposes.

EXAMPLE 21

2-Ethoxyethyl di-(4-chlorophenyl)methyloxyacetate was filled in conventional manner into soft gelatine capsules so that each contained either 250 or 500 mg. of active ingredient together, if desired, with a conventional diluent. There were thus obtained capsules suitable for oral administration for therapeutic purposes.

In a similar manner the active ingredient in the above procedure may be replaced by another compound of formula I which is liquid at ambient temperatures, for example a compound as described in any one of Examples 1, 3–6, 12, 13, 15 or 16.

What we claim is:
1. A sterile pharmaceutical composition in a form suitable for administration in the treatment of arthritic joint diseases and which comprises an effective amount of an acetic acid derivative of the formula

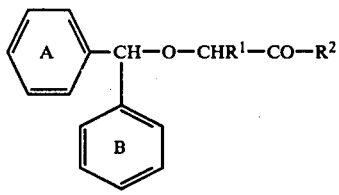

wherein $R^1$ is hydrogen, $R^2$ is a hydroxy or a $C_{1-6}$-alkoxy radical; and ring A and ring B, which may be the same or different, are monohalogenophenyl radicals; or a pharmaceutically acceptable base-addition salt of said derivatives wherein $R^2$ is a hydroxy radical in association with a pharmaceutically acceptable diluent or carrier.

2. A composition as claimed in claim 1 which is in the form of a tablet, capsule, aqueous suspension, oily solution or suspension, emulsion, dispersible powder, granule, syrup or elixir.

3. A composition as claimed in claim 1 in solid dosage form wherein the acetic acid derivative of formula I is selected from the group consisting of di-(4-chlorophenyl) methyloxyacetic acid, di-(2-chlorophenyl)methyloxyacetic acid, and their pharmaceutically acceptable base-addition salts.

4. A method for the treatment of arthritic joint diseases in warm-blooded animals requiring such treatment which comprises administering an effective amount of a composition which comprises an effective amount of an acetic acid derivative of the formula

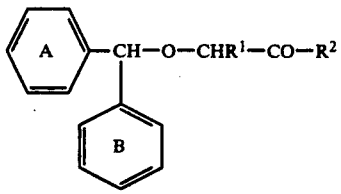

wherein $R^1$ is hydrogen, $R^2$ is a hydroxy or a $C_{1-6}$-alkoxy radical; and ring A and ring B, which may be the same or different, are monohalogenophenyl radicals; or a pharmaceutically acceptable base-addition salt of said derivatives wherein $R^2$ is a hydroxy radical in association with a pharmaceutically acceptable diluent or carrier.

* * * * *